US008965116B2

(12) United States Patent
Ribnick et al.

(10) Patent No.: US 8,965,116 B2
(45) Date of Patent: Feb. 24, 2015

(54) COMPUTER-AIDED ASSIGNMENT OF RATINGS TO DIGITAL SAMPLES OF A MANUFACTURED WEB PRODUCT

(75) Inventors: Evan J. Ribnick, St. Louis Park, MN (US); Kenneth G. Brittain, Cottage Grove, MN (US); Gregory D. Kostuch, Mahtomedi, MN (US); Catherine P. Tarnowski, Mahtomedi, MN (US); Derek H. Justice, Cary, NC (US); Guillermo Sapiro, Durham, NC (US); Sammuel D. Herbert, Woodbury, MN (US); David L. Hofeldt, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 127 days.

(21) Appl. No.: 13/877,545

(22) PCT Filed: Oct. 14, 2011

(86) PCT No.: PCT/US2011/056377
§ 371 (c)(1),
(2), (4) Date: Apr. 3, 2013

(87) PCT Pub. No.: WO2012/054339
PCT Pub. Date: Apr. 26, 2012

(65) Prior Publication Data
US 2013/0202200 A1 Aug. 8, 2013

Related U.S. Application Data

(60) Provisional application No. 61/394,428, filed on Oct. 19, 2010.

(51) Int. Cl.
*G06K 9/00* (2006.01)
*G06K 9/62* (2006.01)
(Continued)

(52) U.S. Cl.
CPC .......... *G06K 9/00536* (2013.01); *G06K 9/6221* (2013.01); *G06K 9/6254* (2013.01);
(Continued)

(58) Field of Classification Search
CPC . G06K 9/6218; G06K 9/6228; G06K 9/6255; G06K 9/68; G06K 9/80; G06T 7/0004; G06T 7/001; G06T 2207/30148; G06T 2207/30164; G06T 7/0006
USPC .................................. 382/160, 141, 159, 149
See application file for complete search history.

(56) References Cited

U.S. PATENT DOCUMENTS

| 5,911,139 A | 6/1999 | Jain et al. |
| 6,445,834 B1 | 9/2002 | Rising, III |

(Continued)

FOREIGN PATENT DOCUMENTS

| JP | 2003-317082 | 11/2003 |
| WO | WO 02/077870 | 10/2002 |
| WO | WO 2010/059679 | 5/2010 |

OTHER PUBLICATIONS

Day et al., "Efficient Algorithms for Agglomerative Hierarchical Clustering Methods", *Journal of Classification*, vol. 1, No. 1, (1984), pp. 7-24.

(Continued)

*Primary Examiner* — Ruiping Li
(74) *Attorney, Agent, or Firm* — James A. Baker

(57) ABSTRACT

A computerized rating tool is described that assists a user in efficiently and consistently assigning expert ratings (i.e., labels) to a large collection of training images representing samples of a given product. The rating tool provides mechanisms for visualizing the training images in an intuitive and configurable fashion, including clustering and ordering the training images. In some embodiments, the rating tool provides an easy-to-use interface for exploring multiple types of defects represented in the data and efficiently assigning expert ratings. In other embodiments, the computer automatically assigns ratings (i.e., labels) to the individual clusters containing the large collection of digital images representing the samples. In addition, the computerized tool has capabilities ideal for labeling very large datasets, including the ability to automatically identify and select a most relevant subset of the images for a defect and to automatically propagate labels from this subset to the remaining images without requiring further user interaction.

20 Claims, 8 Drawing Sheets

(51) Int. Cl.
   *G06T 7/00*      (2006.01)
   *G01N 21/89*     (2006.01)
   *G01N 21/88*     (2006.01)

(52) U.S. Cl.
   CPC .............. *G06T 7/001* (2013.01); *G01N 21/89* (2013.01); *G01N 2021/8854* (2013.01); *G06T 2207/10016* (2013.01); *G06T 2207/20081* (2013.01); *G06T 2207/20084* (2013.01); *G06T 2207/30124* (2013.01)
   USPC ............ 382/160; 382/141; 382/159; 382/149

(56) References Cited

U.S. PATENT DOCUMENTS

| | | | |
|---|---|---|---|
| 6,847,733 B2 | 1/2005 | Savakis et al. | |
| 6,999,614 B1 * | 2/2006 | Bakker et al. | 382/159 |
| 7,023,446 B1 | 4/2006 | Iwasaki | |
| 7,283,659 B1 | 10/2007 | Bakker et al. | |
| 7,359,544 B2 | 4/2008 | Gao et al. | |
| 7,529,732 B2 | 5/2009 | Liu et al. | |
| 2003/0202703 A1 | 10/2003 | Ogi | |
| 2004/0120569 A1 | 6/2004 | Hung et al. | |
| 2005/0135667 A1 | 6/2005 | Saarela et al. | |

OTHER PUBLICATIONS

Tuzel et al., "Region Covariance: A Fast Descriptor for Detection and Classification", Proceedings of the European Conference on Computer Vision, (2006), pp. 589-600.

Zhu et al., "Learning from Labeled and Unlabeled Data with Label Propagation", CMU CALD Technical Report CMU-CALD-02-107, (2002), 19 pages.

* cited by examiner

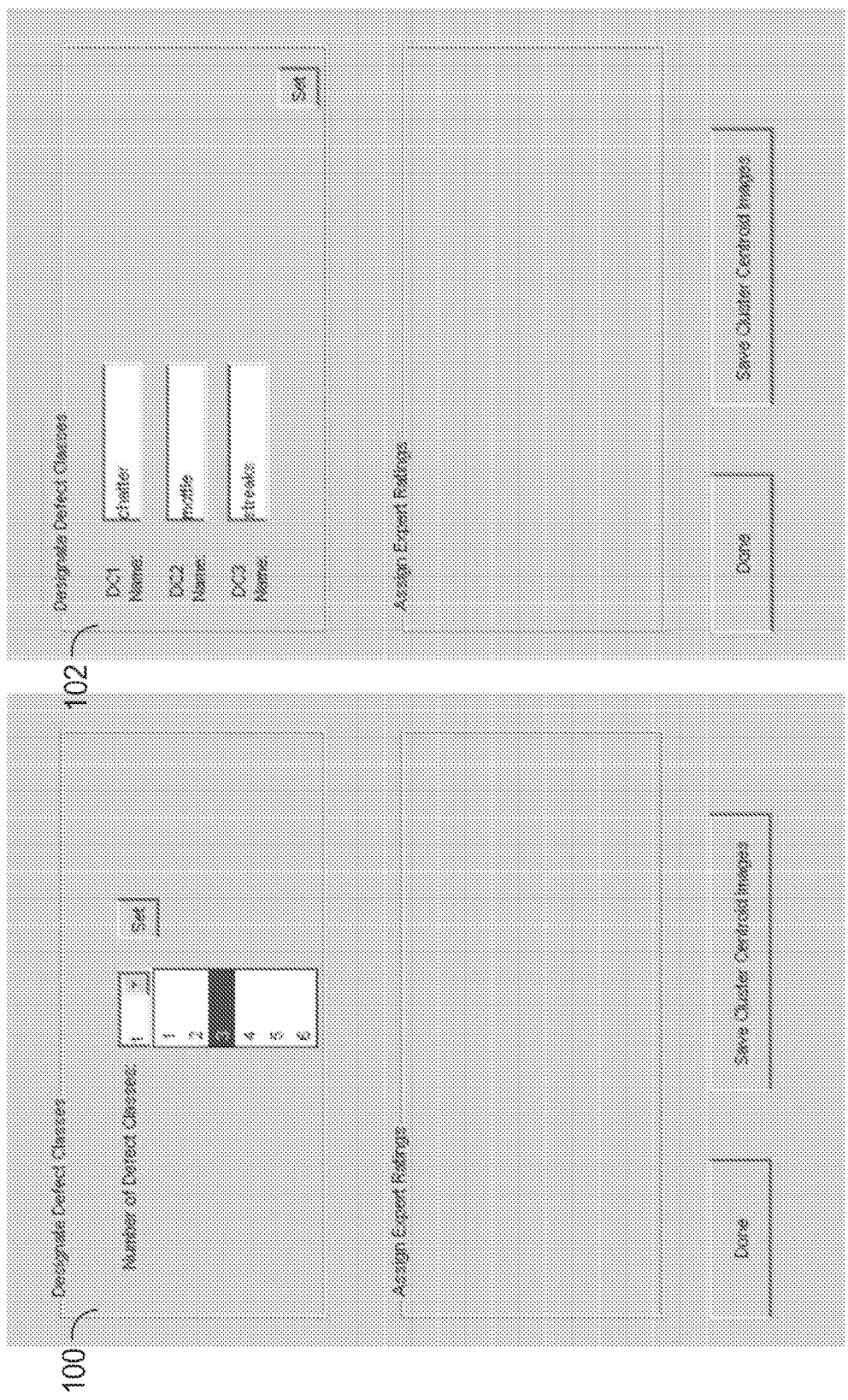

*FIG. 9*

COMPUTER-AIDED ASSIGNMENT OF RATINGS TO DIGITAL SAMPLES OF A MANUFACTURED WEB PRODUCT

CROSS REFERENCE TO RELATED APPLICATION

This application claims the benefit of U.S. Provisional Patent Application No. 61/394,428, filed Oct. 19, 2010, the disclosure of which is incorporated by reference herein in its entirety.

TECHNICAL FIELD

The invention relates to automated inspection systems, such as computerized systems for inspection of moving webs.

BACKGROUND

Computerized inspection systems for the analysis of moving web materials have proven critical to modern manufacturing operations. For example, it is becoming increasingly common to deploy imaging-based inspection systems that can automatically classify the quality of a manufactured product based on digital images captured by optical inspection sensors (e.g., cameras). These inspection systems typically rely on complex technologies such as machine learning, pattern recognition, and computer vision.

Some inspection systems apply algorithms, which are often referred to as "classifiers," that assign a rating to each captured digital image (i.e., "sample") indicating whether the sample is acceptable or unacceptable, in the simplest case, or a more sophisticated set of labels corresponding to degrees of variation or level of quality. These types of inspection systems usually proceed in two separate phases of processing.

The first step, which is performed offline, is referred to as the "training phase." During the training phase, a set of representative sample images are manually assigned ratings (also referred to herein as "labels") by a set of experts. The experts may be, for example, process engineers that have significant experience in manually inspecting web products and identifying potential defects. Based on the sample images, a classification model is developed for the training data that can be used by the computerized inspection system. In this way, the training phase can be thought of as the learning part of the inspection process.

Once the model has been developed from the training data, it can be applied to new samples captured from newly manufactured product, potentially in real-time, during the "classification phase" of the processing. That is, the classification model can be used online by the computerized web inspection system to classify new sample images by assigning each of the samples a label.

The ability of the computerized inspection system to correctly rate new sample images is directly related to the quality and accuracy of the initial training data used to train the system, i.e., the sample images and their corresponding, labels assigned by the experts. For example, the samples in the training set should be representative of the entire distribution of data that is expected to be obtained from a given web application. As such, it is generally advantageous to have a large number of training samples, which can help to train a model more effectively and to reduce the effects of overfitting, which is characterized by a model that it distinguishes noise or other insignificant differences between training samples and has poor predictive performance outside of the training sample set. However, the task of manually labeling large numbers of samples can be extremely time consuming and tedious for the experts. Worse still is the fact that this labeling is subjective, and an expert who is intimately familiar with the product may produce inconsistent labels due to the nature of the task. Furthermore, inconsistencies may arise between different expert raters. These difficulties are amplified as the size the training set grows and are compounded by the fact that the same web material may be applied in different end-uses, which have different acceptance tolerances. As a result, a product that might be deemed unacceptable for one end-use could be acceptable for another end-use.

SUMMARY

In general, this disclosure describes a computerized rating tool that can assist a user in efficiently and consistently assigning expert ratings (i.e., labels) to a large collection of digital images representing samples of a given product. As one example, the labels may correspond to a severity of a particular non-uniformity defect present in the sample. Instead of the user having to label each sample individually, which can be tedious, subjective, and error-prone, and may result in inconsistent labeling, the computerized tool simplifies the task by automating the most cumbersome aspects, while providing the user with intuitive visual feedback and means for interacting with the data. In some exemplary embodiments, the computerized tool displays the images to the user in a visually appealing manner and eases the task of assigning consistent labels by allowing the user to spatially visualize relationships between samples. In other embodiments, the computer automatically assigns ratings (i.e., labels) to the large collection of digital images representing the samples.

In some exemplary embodiments, the described computerized rating tool provides mechanisms for visualizing the data in an intuitive and configurable fashion, including clustering and ordering the images. In certain exemplary embodiments, the computerized tool provides an easy-to-use interface for exploring multiple types of defects represented in the data and efficiently assigning expert ratings. In addition, the computerized tool has capabilities ideal for labeling very large datasets, including the ability to automatically identify and select a most relevant subset of the images for a defect and to automatically propagate labels from this subset to the remaining images without requiring further user interaction.

In one exemplary embodiment, an apparatus comprises a processor or computer including a processor, a memory storing a plurality of training samples and rating software executing on the processor. The rating software includes a feature extraction module to extract features from each of a plurality of training images by computing a numerical descriptor for each of the training images from pixel values of the respective training image. The rating software performs a first clustering process to process the numerical descriptors of the training images to automatically select a representative subset of the training images and compute a plurality of image clusters for the representative subset of training images.

In some exemplary embodiments, at least one of the rating software executing on the processor or a user interface presented by the rating software and providing input mechanisms to receive input from a user, specifies one or more classes of defects present within the representative training images and a set of rating labels for each of the classes of defects. In certain exemplary embodiments, the user interface includes input mechanisms to receive input assigning an individual rating label to each of the image clusters for each of the specified classes of defects.

In additional or alternative exemplary embodiments, the processor or computer is used to determine a number of defect classes present within the representative training images and assign a severity label to each of the plurality of image clusters for each of the specified classes of defects. In some particular exemplary embodiments, the rating software executing on the processor specifies a number of defect classes present within the representative training images, and assigns a severity label to each of the plurality of image clusters for each of the specified classes of defects.

In any of the foregoing exemplary embodiments, the rating software may automatically propagate each of the individual rating labels assigned to the classes of defects for each of the image clusters to all of the training images within that image cluster.

In further embodiments, the method comprises executing rating software on a computer to extract features from each of a plurality of training images by computing a numerical descriptor for each of the training images from pixel values of the respective training image. The method further comprises processing the numerical descriptors of the training images with the rating software to automatically select a representative subset of the training images, and performing a first clustering process with the rating software to process the numerical descriptors of the representative subset of the training images and compute a plurality of image clusters for the representative subset of training images.

In some exemplary embodiments, rating software executing on the processor, wherein the rating software includes a feature extraction module to extract features from each of a plurality of training images by computing a numerical descriptor for each of the training images from pixel values of the respective training image, and wherein the rating software performs a first clustering process to process the numerical descriptors of the training images to automatically select a representative subset of the training images and compute a plurality of image clusters for the representative subset of training images. At least one of the rating software executing on the processor or a user interface presented by the rating software and having input mechanisms to receive input from a user, specifies one or more classes of defects present within the representative training images and a set of individual rating labels for each of the classes of defects.

Thus, in some particular exemplary embodiments, the method further comprises presenting a user interface with the rating software to receive input from a user specifying one or more classes of defects present within the representative training images and a set of rating labels for each of the classes of defects; receiving input assigning an individual rating label to each of the image clusters for each of the specified classes of defects; and, for each of the image clusters, automatically propagating, with the rating software, each of the individual rating labels assigned to the classes of defects for the image cluster to all of the training images within that image cluster.

However, in other additional or alternative exemplary embodiments, the method further comprises receiving input from the computer specifying one or more classes of defects present within the representative training images and a set of rating labels for each of the classes of defects. In certain such embodiments, receiving input from the computer further comprises using the computer to determine a number of defect classes present within the representative training images and assign a severity label to each of the plurality of image clusters for each of the specified classes of defects.

The techniques may provide one or more advantages. For example, in light of the inherent problems with manually labeling large sets of training data, the computerized tool described herein automates parts of this tedious process of labeling large datasets, while still keeping the human in the loop in a way that makes efficient use of his or her expertise. This may allow the model developed via the training phase of supervised/semi-supervised classification algorithms to be successfully applied by computerized inspection systems.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 4-9 illustrate example features of a user interface presented by the rating tool.

DETAILED DESCRIPTION

Figure 1:
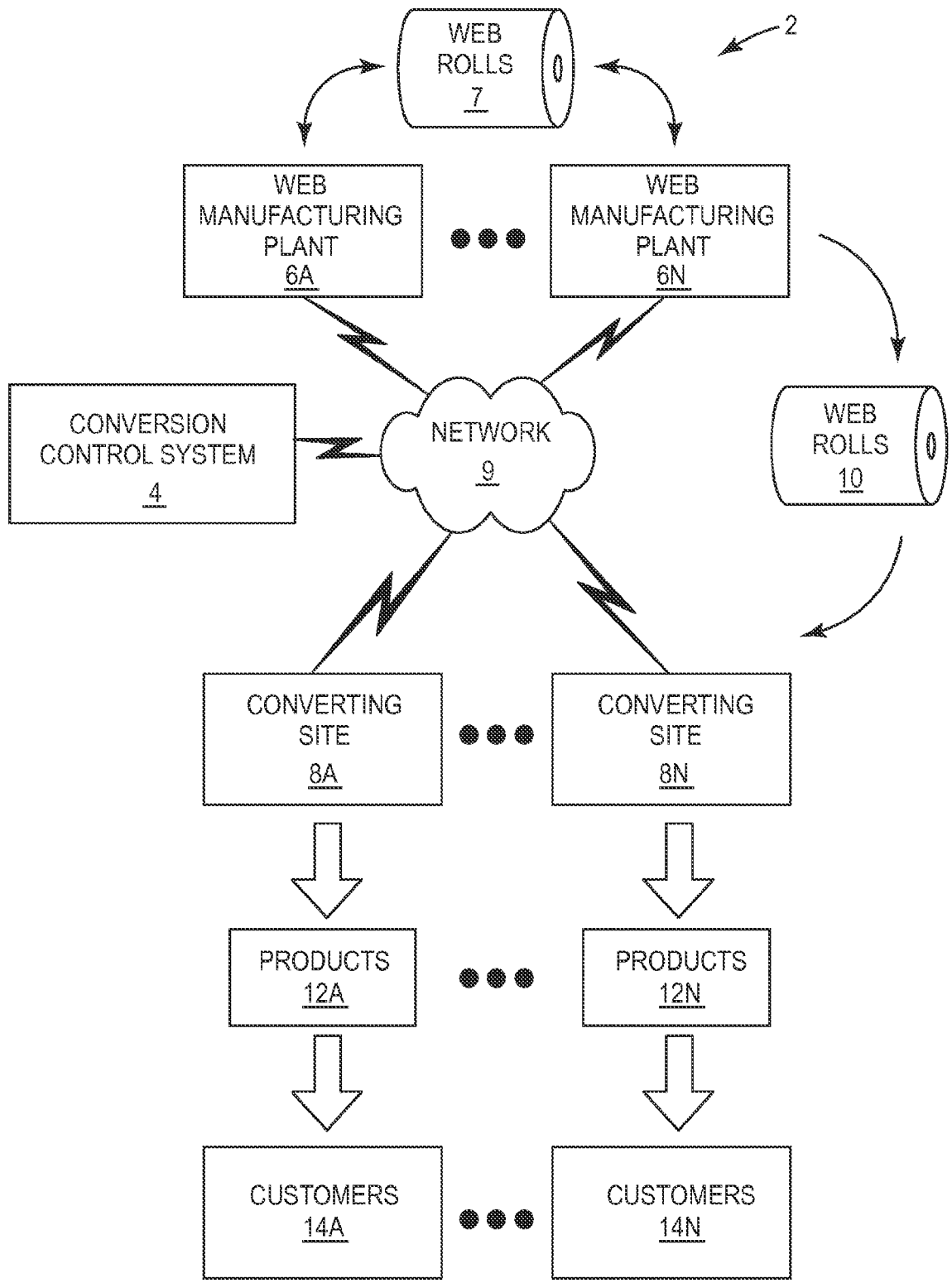
FIG. 1 is a block diagram illustrating an example web manufacturing and conversion system in which the techniques described herein may be applied.

FIG. 1 is a block diagram illustrating an example system 2 in which the techniques described herein may be applied. Web manufacturing plants 6A-6N (web manufacturing plants 6) represent manufacturing sites that produce and ship web material in the form of web rolls 7. Web manufacturing plants 6 may be geographically distributed, and each of the web manufacturing plants may include one or more manufacturing process lines. In general, web rolls 7 may be manufactured by any of manufacturing plants 6 and shipped between the web manufacturing plants for additional processing. Finished web rolls 10 are shipped to converting sites 8A-8N (converting sites 8) for conversion into products 12A-12N (products 12). As shown in FIG. 1, conversion control system 4, web manufacturing plants 6A-6M (web manufacturing plants 6) and converting sites 8A-8N (converting sites 8) are interconnected by a computer network 9 for exchanging information (e.g., defect information) related to manufacture of the web material and conversion into products 12.

In general, web rolls 7, 10 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

Converting sites 8 may receive finished web rolls 10 from web manufacturing plants 6 and convert finished web rolls 10 into individual sheets for incorporation into products 12 for sale to customers 14A-14N (customers 14). Converting systems may determine into which products 14 a given finished web roll 10 is converted based on a variety of criteria, such as grade levels associated with the product. That is, the selection process of which sheets should be incorporated into which products 12 may be based on the specific grade levels each sheet satisfies. In accordance with the techniques described herein, converting sites 8 may also receive data regarding anomalies, i.e. potential defects, in the finished web rolls 10. Ultimately, converting sites 8 may convert finished web rolls 10 into individual sheets which may be incorporated into products 12 for sale to customers 14A-14N (customers 14).

In order to produce a finished web roll 10 that is ready for conversion into individual sheets for incorporation into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced. For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof.

Figure 2:
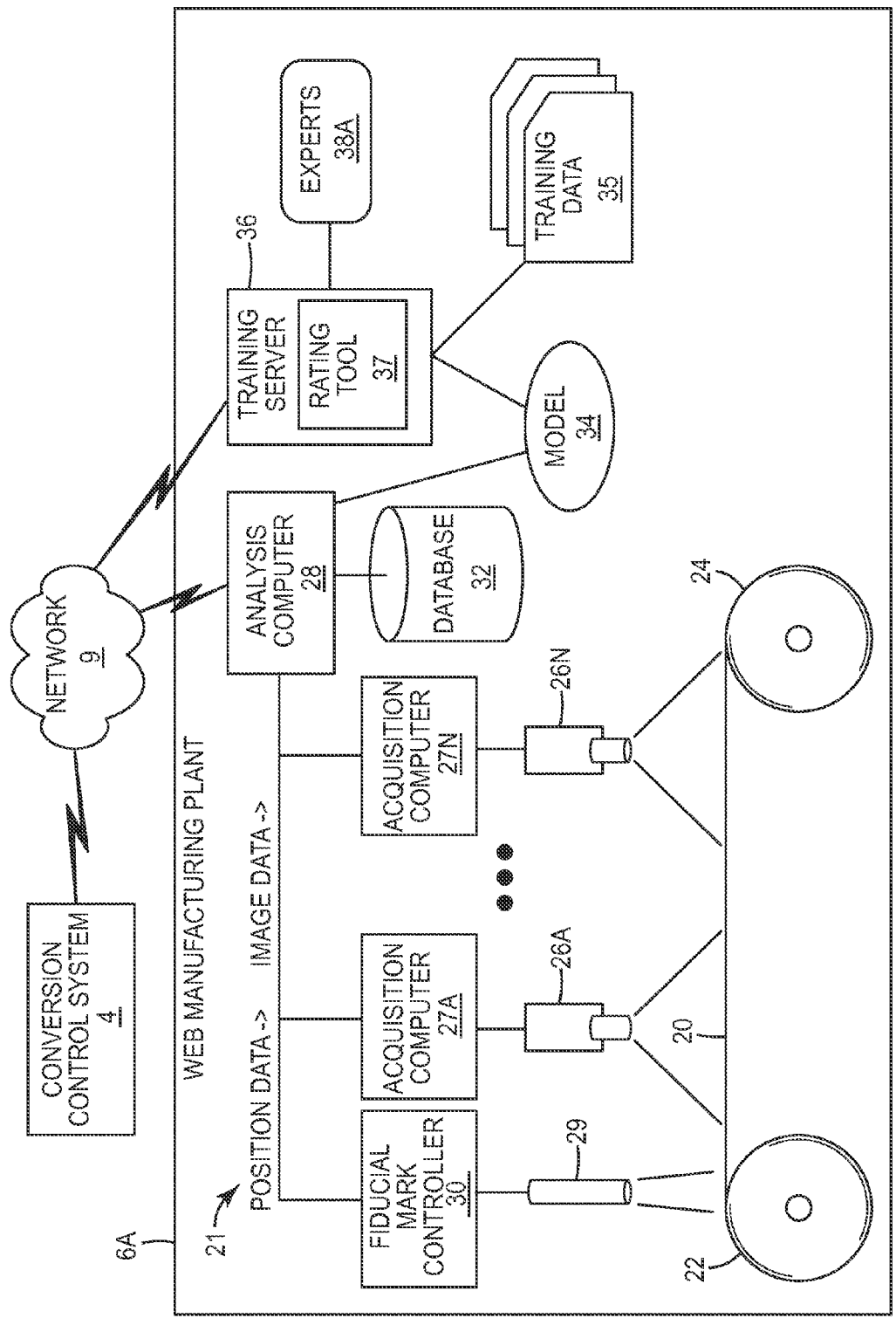
FIG. 2 is a block diagram illustrating an exemplary embodiment of an inspection system in an exemplary web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital images. The inspection systems may analyze the images with one or more algorithms to produce so-called "local" anomaly information that may represent an actual "defect" depending upon the ultimate product 12 into which the web is converted. The inspection systems may, for example, produce anomaly information for "point" defects in which each defect is localized to a single area. As another example, the inspections systems may produce anomaly information for "non-uniform" defects or "non-uniformities" in which the web material exhibits non-uniform variability over a large area. Examples of such non-uniformities include mottle, chatter, banding, and streaks.

Analysis computers within web manufacturing plants may apply algorithms, referred to herein as "classifiers," that assign a quality rating (i.e., label) to each captured digital image (i.e., "sample"). The analysis computers may apply the algorithms in real-time as the web is manufactured or offline after all image data has been captured for the web. In either case, the labels classify each corresponding region of the web into a quality level. In one example, the labels classify each region as either acceptable or unacceptable. As another example, the classifiers may assign a sophisticated set of labels corresponding to degrees of variation. The assigned labels may ultimately be used to accept or reject the regions of the web material based on the particular products 12 to which the web is being converted.

During the classification process, the analysis computers classify the captured digital images by application of a classification model that has been developed based on training data. The training data is typically processed during a "training phase" of the algorithms and the classification model is developed to best match the training data. That is, after the training phase and development of the classification model, application of the classification model to the training data will label the training data with a high probability of correctness. Once the model has been developed from the training data, the analysis computers apply the model to samples captured from newly manufactured product, potentially in real-time, during the "classification phase" of the processing.

In some embodiments, classification of digital images for a given manufactured web may be performed offline by conversion control system 4. Based on the classifications for a given web, conversion control system 4 may select and generate a conversion plan for each web roll 10. The classifications may be application-specific in that a certain anomaly may result in a defect in one product, e.g., product 12A, whereas the anomaly may not cause a defect in a different product, e.g., product 12B. Each conversion plan represents defined instructions for processing a corresponding finished web roll 10 for creating products 12, which may ultimately be sold to customers 14. For example, a web roll 10 may be converted into final products, e.g., sheets of a certain size, for application to displays of notebook computers. As another example, the same web roll 10 may instead be converted into final products for application to displays of cell phones. Conversion control system 4 may identify which product best achieves certain parameters, such as a maximum utilization of the web, in view of the different defect detection algorithms that may be applied to the anomalies.

FIG. 2 is a block diagram illustrating an exemplary embodiment of an inspection system located within a portion of a web process line 21 in exemplary web manufacturing plant 6A of FIG. 1. In the exemplary embodiment, a segment of a web 20 is positioned between two support rolls 22, 24. Image acquisition devices 26A-26N (image acquisition devices 26) are positioned in close proximity to the continuously moving web 20 and scan sequential portions of the continuously moving web 20 to obtain image data. Acquisition computers 27 collect image data from image acquisition devices 26 and transmit the image data to analysis computer 28.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners, may be utilized as the imaging acquisition device. A sequential portion of the web indicates that the data is acquired by a succession of single lines. Single lines comprise an area of the continuously moving web that maps to a single row of sensor elements or pixels. Examples of devices suitable for acquiring the image include linescan cameras such as Piranha Models from Dalsa (Waterloo, Ontario, Canada), or Model Aviiva SC2 CL from Atmel (San Jose, Calif.). Additional examples include laser scanners from Surface Inspection Systems GmbH (Munich, Germany) in conjunction with an analog to digital converter.

The image data may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

In some embodiments, fiducial mark controller 30 controls fiducial mark reader 29 to collect roll and position information from web 20. For example, fiducial mark controller 30 may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. Fiducial mark controller 30 communicates the roll and position information to analysis computer 28 for association with detected anomalies.

Analysis computer 28 processes streams of image data from acquisition computers 27. That is, in accordance with the techniques described herein, analysis computer 28 apply classifiers to assign a quality rating (i.e., label) to each captured digital image in accordance with classification model 34 ("model 34") that has been developed based on training data 35. Further details on classifiers and classifier construction are described in PCT International Application Publication No. WO 2010/059679.

Training data 35 typically consists of a large set of representative sample digital images that have been assigned ratings by one or more experts 38. The digital images may, for example, represent samples taken from web 20 or another web previously produced by web process line 21.

Thus, in some exemplary embodiments, training server 36 provides an operating environment for execution of software that provides a computerized expert rating tool 37 ("rating tool 37") to assist experts 38 in efficiently and consistently assigning ratings (i.e., labels) to the large collection of digital images representing the samples. That is, one or more experts 38 interact with a user interface presented by expert rating tool 37 to assign a quality rating to each digital image of the sample set. As described in further detail herein, expert rating tool 37 provides a user interface that allows one or more experts 38 to visualize and modify clusters of images within training data 35, explore the training data in order to identify the represented types of defects, and assign expert ratings to the images.

More specifically, expert rating tool 37 provides mechanisms for visualizing the data in an intuitive and configurable fashion, including features for clustering and ordering the sample images. Expert rating tool 37 also provides an easy-to-use interface for exploring multiple types of defects represented in the data and efficiently assigning expert ratings. In addition, expert rating tool 37 has capabilities ideal for labeling very large datasets, including the ability to automatically identify and select a most relevant subset of the images for a defect and to propagate labels from this subset to the remaining images without requiring further user interaction. This may allow the results of the training phase of supervised/semi-supervised classification algorithms to be successfully applied by the computerized inspection systems within manufacturing plants 6. Experts 38 may interact directly with training server 36 via a local user interface (e.g., experts 38A within manufacturing plant 6A) or remotely by way of network 9 (e.g., experts 38B).

In other exemplary embodiments, it may be desirable to additionally or alternatively have the computer automatically assign ratings (i.e., labels) to the large collection of digital images representing the samples. For example, training server 36 may provide an operating environment for execution of software that automatically assigns a quality rating to each digital image of the sample set, for example, by grouping together similar images into defect classes based on the number of defects observed in each image, thereby providing an estimate of the number of defect classes automatically. This could be done, for example, by comparing the features extracted from the images and computing their similarities. Once this is done, an initial estimate of a label could also be assigned automatically to an image in each of the defect classes, for example by comparing the image to other images exhibiting the defect, and estimating the severity exhibited in the current image with respect to the others.

Expert rating tool 37 may be implemented, at least in part or even entirely, as software instructions executed by one or more processors of training server 36, including one or more hardware microprocessors, digital signal processors (DSPs), application specific integrated circuits (ASICs), field programmable gate arrays (FPGAs), or any other equivalent integrated or discrete logic circuitry, as well as any combinations of such components. The software instructions may be stored within in a non-transitory computer readable medium, such as random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media.

Although shown for purposes of example as positioned within manufacturing plant 6A, training server 36 and rating tool 37 may be located external to the manufacturing plant, e.g., at a central location or at a converting site. For example, training server 36 and rating tool 37 may operate within conversion control system 4. In this example, training server 36 communicates classification model 34 to analysis computer 28 for application to samples collected from web material 20.

Once training data 35 and classification model 34 has been established, training server 36 processes the training data to generate model 34 for subsequent use for real-time analysis and classification of image data received from acquisition computers 27 for web material 20. In this way, new images of regions of web material 20 can be classified in accordance with classification model 34. Analysis computer 28 may utilize any technology that may make use of expertly-rated training data 35, such as machine learning including neural networks, adaptive control, data mining, genetic programming, cluster analysis, principal component analysis, pattern recognition, and computer vision. Example defects that may be detected include non-uniformities such as mottle, chatter, banding, and streaks, as well as point defects including spots, scratches, and oil drips.

Analysis computer 28 stores the anomaly information for web 20, including roll identifying information for the web 20 and position information for each anomaly, within database 32. For example, analysis computer 28 may utilize position data produced by fiducial mark controller 30 to determine the spatial position or image region of each anomaly within the coordinate system of the process line. That is, based on the position data from fiducial mark controller 30, analysis computer 28 determines the x, y, and possibly z position or range for each anomaly within the coordinate system used by the current process line. For example, a coordinate system may be defined such that the x dimension represents a distance across web 20, a y dimension represents a distance along a length of the web, an the z dimension represents a height of the web, which may be based on the number of coatings, materials or other layers previously applied to the web.

Moreover, an origin for the x, y, z coordinate system may be defined at a physical location within the process line, and is typically associated with an initial feed placement of the web 20. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL Server™ from Microsoft Corporation.

Once the process has ended, analysis computer 28 may transmit the data collected in database 32 to conversion control system 4 via network 9. For example, analysis computer 28 may communicate the roll information as well as the anomaly information and respective sub-images for each anomaly to conversion control system 4 for subsequent, offline, detailed analysis in accordance with classification model 34. For example, the information may be communicated by way of database synchronization between database 32 and conversion control system 4. In some embodiments, conversion control system 4 may determine those products of products 12 for which each anomaly may cause a defect, rather than analysis computer 28. Once data for the finished web roll 10 has been collected in database 32, the data may be communicated to converting sites 8 and/or used to mark anomalies on the web roll, either directly on the surface of the web with a removable or washable mark, or on a cover sheet that may be applied to the web before or during marking of anomalies on the web.

Figure 3:
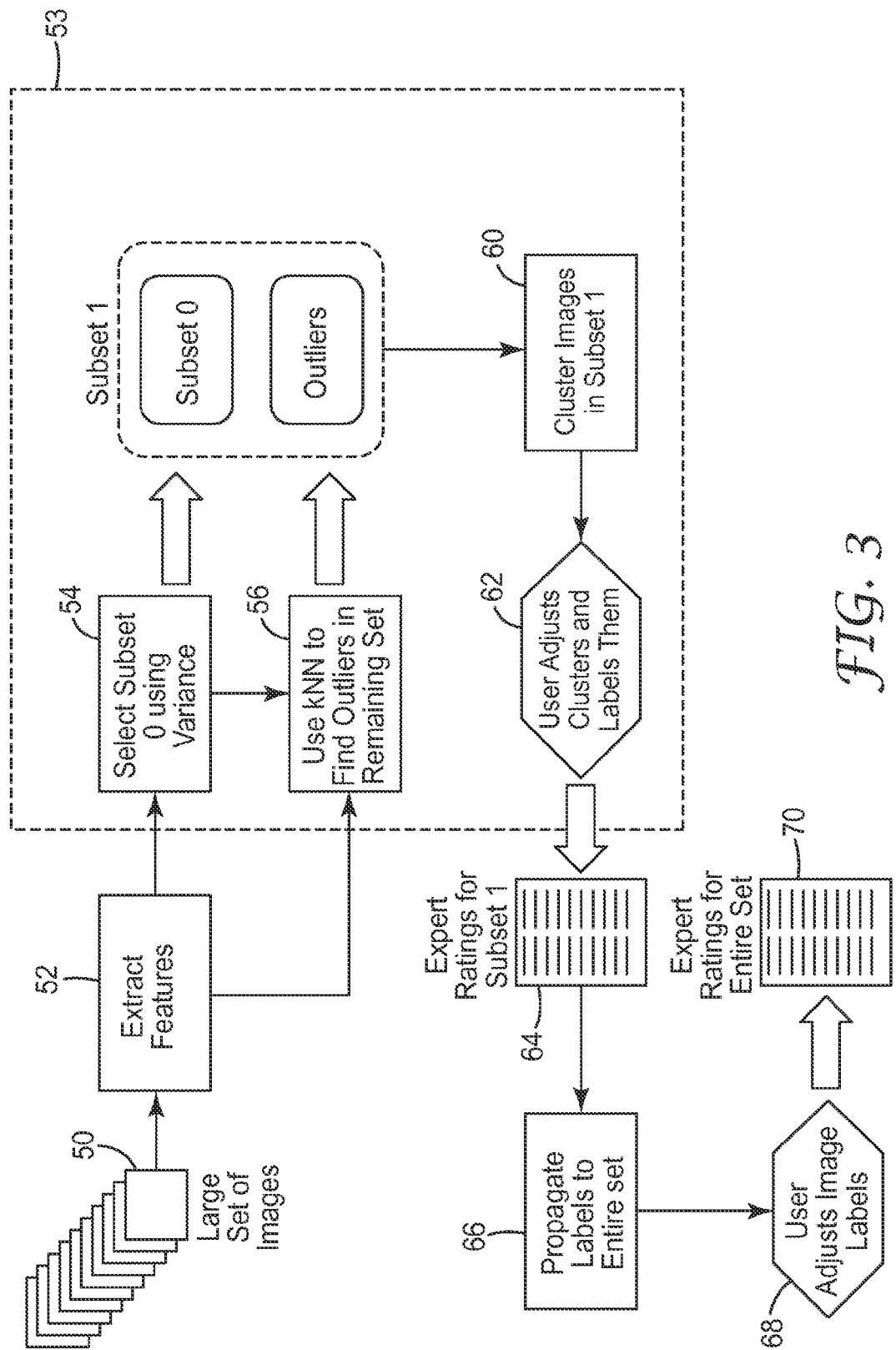
FIG. 3 is a flowchart illustrating an example operation of a software rating tool.

FIG. 3 is a flowchart illustrating an example operation of rating tool 37. Initially, rating tool 37 receives training data 35 as input, typically in the form of a set of images (50). Next, a feature extraction software module of rating tool 37 processes each of the images to extract features (52). Feature extraction provides a numerical descriptor of each of the images as a compact numerical representation of the relevant information inherent in each image. Features can be extracted in any way that preserves useful information about the relationships between images in the training set, and at the same time eliminates un-informative image characteristics.

Examples of common feature extraction techniques include convolving the image with a set of filters and computing statistics of the filtered images, or extracting features based on color or intensity histograms. Sometimes the pixel values can be used as features, although in this case there is no compactness in the descriptor, since the entire image must typically be stored. In general, the resulting features are treated as compact descriptions of the relevant information in the corresponding images. In one embodiment, the features are specific to a particular application but instead provide a rich set of features from which different applications can use different feature sub-sets. That is, in this example, the features are not extracted through the use of complicated, application-specific filters. Rather, the filters only facilitate direct pair-wise comparisons between images in order to measure their similarity. Rating tool 37 is not limited to use with any particular feature extraction methodology, and may readily be applied to applications in which other types of features are more appropriate.

One exemplary way to encapsulate the relevant image information in a compact form, particularly as it relates to texture, is to compute a small covariance matrix of pixel features across the image. Once this small covariance matrix (e.g., 5×5) is extracted, pair-wise comparisons between images can be made efficiently based only on these matrices, instead of dealing with the images directly. For example, a grayscale image is defined as a two-dimensional array, indexed by pixel coordinates x and y, as l(x, y). At each pixel location (x, y), a feature vector is extracted based on the intensity values of the pixel and their first and second derivatives at that pixel:

$$f(x, y) = \left( I(x, y) \quad \frac{\partial I(x, y)}{\partial x} \quad \frac{\partial I(x, y)}{\partial y} \quad \frac{\partial^2 I(x, y)}{\partial x^2} \quad \frac{\partial^2 I(x, y)}{\partial y^2} \right)^T. \quad (1)$$

Image derivatives (gradients) can be approximated simply by computing forward or central differences between intensity values at each pixel. Finally, the covariance matrix of these pixel features is computed across the entire image:

$$C_I = \frac{1}{N-1} \sum_{(x,y) \in I} (f(x, y) - \mu)(f(x, y) - \mu)^T, \quad (2)$$

where N is the number of pixels in the image, and:

$$\mu = \frac{1}{N} \sum_{(x,y) \in I} f(x, y) \quad (3)$$

is the mean of the pixel features. In subsequent processing steps, including the clustering phase of the algorithm, it may be useful to compute pair-wise distances between images. In the case of these covariance matrix descriptors, pair-wise distances are computed as:

$$d_C(I_1, I_2) = \sqrt{\sum_{i=1}^{5} \ln^2 \lambda_i(C_{I_1}, C_{I_2})}, \quad (4)$$

where $\lambda_i(C_{I1}; C_{I2})$ is the ith generalized eigenvalue of the two covariance matrices.

Further details can be found in O. Tuzel, F. Porikli, and P. Meer. "Region Covariance: A Fast Descriptor for Detection and Classification." Proceedings of the European Conference on Computer Vision, 2006, incorporated herein by reference.

After extracting features for each of the training images, rating tool 37 enters a clustering phase (53) in which the images are clustered based on the descriptive features extracted from the images. It is not uncommon for sets of images used for training and testing classification algorithms to be very large, often on the order of tens of thousands of images. Clustering and visualizing in detail this many images is typically not practical in a short period of time and may furthermore be unnecessary, since most large datasets contain significant redundancy, so that only a representative subset needs to be analyzed in detail.

In some exemplary embodiments, the computer or processor automatically receives information from software executing on the computer or processor which specifies one or more classes of defects present within the representative training images and a set of rating labels for each of the classes of defects. Thus, in certain such embodiments, the computer or processor executes software (e.g. rating tool 37) that is used to determine a number of defect classes present within the representative training images and assign a severity label to each of the plurality of image clusters for each of the specified classes of defects. In some particular exemplary embodiments, the rating software executing on the computer or processor specifies a number of defect classes present within the representative training images, and assigns a severity label to each of the plurality of image clusters for each of the specified classes of defects.

In certain exemplary embodiments, one or both of the determination of the number of defect types present and the assignment of severity labels to images in each of those defect classes can be received as user input, and/or received as input from the computer, for example, by executing software on the computer or processor to automatically calculate or estimate all or a portion of those inputs. However, it will be understood by one of ordinary skill in the art that receiving input from the computer could be accomplished in various ways.

As one example referred to herein as the Angle Quantization method, the computer may receive input by executing the following steps, which may be carried out in any order unless constrained or limited to a particular order by another step. The first steps (described further above) comprise selecting a representative subset of images to process, extracting a descriptive numerical feature vector from each of these images, and clustering them. The number of defect types present can be estimated by software executing on the computer or processor by first computing the centroid of all the images in feature space, referred to as the global centroid (i.e., the mean of the feature descriptors extracted from all the images), and then computing the angle of the vector from the global centroid to the centroid of each individual cluster, as compared to the vector for the other clusters. When a set of possibly multiple clusters is found to have vectors with very small angles between them, it can be assumed that this set of clusters represents images with a single type of defect. Identifying all such sets of clusters with vectors with small angles between them will determine the number of defect types present.

Once each type of defect is identified, it can be represented by a single vector originating from the global centroid, computed by first normalizing the vectors of the clusters comprising this defect type, and then computing their mean. Finally, the severity label of an image in a given defect class can be estimated automatically by computing the projection of this image's vector (from the global centroid to this image in feature space) onto the representative vector for the particular defect type, where the defect severity is given by the length of this projection.

As another example referred to herein as the Topic Modeling method, the computer may receive input by executing the following steps, which may be carried out in any order unless constrained or limited to a particular order by another step. Once the images are clustered as in the Angle Quantization method, each image (or the centroid of each cluster, if there are a large number of them) is divided into square patches of a specified size. Image formation is then modeled as a generative probabilistic process, the objective of which is to attempt to model as accurately as possible the theoretical process by which images were generated. According to this generative model, each image is constructed from a mixture of defect types, each of which will influence which patches are chosen to construct this image. The parameters governing this generative process are learned from the images using, for example, a probabilistic inference technique such as Markov Chain Monte Carlo sampling. The results of this inference will produce a model of the various types of defects found in these images, where each image in the set has been modeled as some mixture of these defects. This will also provide a means for measuring the contribution (i.e., severity level) of each defect type in a given image.

In additional or alternative exemplary embodiments, one or more experts 38 interact with a user interface presented by expert rating tool 37 to assign a quality rating to each digital image of the sample set, and rating tool 37 automatically selects a representative subset of the images to aid expert 38 in the labeling process (54). To assist expert 38 in actively exploring the data and identifying the types of defects present, rating tool 37 automatically selects the subset so as to contain extreme examples of the different types of defects present within training data 35, as well as examples of images with normal levels of defectiveness.

In one such exemplary embodiment, rating tool 37 utilizes variance of pixel intensities for distinguishing cases of relatively extreme defectiveness, which has been observed to be sufficient in characterizing non-uniformities (i.e., textures) in images of web-based products. Furthermore, computing pixel variance is relatively computationally inexpensive, which may be advantageous for very large sets of training images. In the case the covariance matrix descriptors outlined above, the pixel intensity variance is given in the upper-left element of the matrix $C_1$, so that no additional computation is necessary. In this example, the first step in selecting a subset is to identify the $N_1$ images with the highest variance (54). These roughly correspond to the $N_1$ most defective images in the training data 35. Since it is also important for the subset to be representative of the set as a whole, rating tool 37 also selects $N_2$ images randomly from the remaining set. This set of $N_1+N_2$ images comprises the initial subset $S_0$ (denoted "subset 0" in FIG. 3). The sizes $N_1$ and $N_2$ are selected by the user.

In addition, rating tool 37 generates the subset to include any outliers not already included in $S_0$ that are not well represented by $S_0$ (56). Each remaining image not in $S_0$ is processed to identify its k nearest-neighbors (kNNs) in a feature space using the distance function described above (eq. 4). The term "feature space" refers to the multi-dimensional space defined by the dimensions of a feature vector, such as the feature vector defined above in eq. 1. If the distances to all of its kNNs are greater than a threshold $T_d$, then the image is considered an outlier. The parameters k and $T_d$ can be configured by expert 38, although default values may be used. This allows expert 38 to try different values and view the results. Example default values may be, for example, k=5 and $T_d=1.0$. Rating tool 37 adds any outliers selected in this manner to the previously selected $N_1+N_2$ images to form the complete subset $S_1$ (denoted "subset 1" in FIG. 1).

After selecting representative subset $S_1$ of training images, rating tool 37 applies a clustering algorithm to the subset to form small groups of relatively similar images from those in subset $S_1$ (60). Rating tool 37 forms the clusters to present a more intuitive visualization of the training dataset and makes it easier for expert 38 to explore. In one example, rating tool 37 applies a bottom-up agglomerative clustering algorithm to form image clusters in subset $S_1$ according to their covariance matrix descriptors. In this process, each image is initially treated as a separate cluster and successive clusters are identified using previously established clusters. For example, based on the inter-image distances computed using (4), rating tool 37 forms an agglomerative hierarchical linkage tree, which encapsulates the hierarchical inter-relationships between the training data. Rating tree terminates the process (i.e., "cuts off" the linkage tree) at a certain point in order to generate the configured number of clusters $N_c$, as specified by expert 38. Additional information on agglomerative hierarchical clustering can be found in W. H. E. Day and H. Edelsbrunner, "Efficient Algorithms for Agglomerative Hierarchical Clustering Methods."*Journal of Classification, vol.* 1, no. 1, pp. 7-24, 1984.

Since there may be many clusters (e.g., several hundred in some cases), rating tool 37 also orders the clusters with respect to one another so that the most similar groups are displayed in close proximity to one another. This is accomplished by rating tool 37 forming a second agglomerative hierarchical linkage tree, in this case encapsulating the inter-relationships between the clusters themselves. Thus, an ordering of the clusters can be obtained by observing the lowest level (leaf nodes) of the second tree. To form the second hierarchical linkage tree, rating tree 37 analyzes the image clusters in pair-wise fashion and computes pairwise inter-cluster distances between each cluster pair. The inter-cluster distances between each of the clusters is used to form the second linkage tree. In one example, rating tree 37 computes the distance between two clusters as the median of the individual distances between the images in the two clusters. Rating tool 37 utilizes the arrangement of the leaf nodes of the second tree to control display of the image clusters, thereby displaying the most similar image clusters in close spatial proximity to one another. This aids expert 38 in forming an understanding of the defects present within and represented by the training data.

In some exemplary embodiments, after clustering the training images by developing the linkage trees, rating tool 37 presents a user interface by which the expert is given an opportunity to visualize the clusters and re-assign images in cases where the clustering is visually unacceptable (62). The user then assigns expert ratings to each cluster of images as opposed to labeling each image independently (64), and rating tool 37 propagates these expert ratings to the remaining set of images without requiring further user interaction, thus resulting in expert ratings for the entire dataset (66). That is, the rating tool 37 applies algorithms described herein to automatically assign expert ratings to the entire dataset of training images. In other words, expert 38 need only assign expert ratings to all (or some) of the image clusters in the subset $S_1$, in each identified defect class, using the user interface provided by rating tool 37.

Rating tool 37 automatically propagates these expert ratings to the remaining unlabeled images, including those images not within in subset $S_1$. For each unlabeled image $I_u$, rating tool 37 computes the pairwise distances from this image to each labeled image $I_l$ (i.e., to each image within subset $S_1$ to which an expert ratings has been assigned) using the distance function (eq. 4). These distances are then converted to pairwise affinities according to:

$$a(I_u, I_\ell) = \exp\left(-\frac{d_C^2(I_u, I_\ell)}{\sigma^2}\right), \quad (5)$$

where the bandwidth parameter $\sigma$ is chosen according to a heuristic operating on the distances $d_c^2(I_u, I_l)$. These affinities are normalized to weights:

$$w(I_u, I_\ell) = P(I_u \to I_\ell) = \frac{a(I_u, I_\ell)}{\sum_i a(I_u, I_\ell)}. \quad (6)$$

The quantity $w(I_u, I_l)$ corresponds to the probability of transitioning from image $I_u$ to image $I_l$ in a random walk through feature space and w is normalized such that $\Sigma_i w(I_u, I_{li})=1$.

Finally, the probability of image $I_u$ belonging to the expert rating e in this defect class is computed as:

$$p_e(I_u) = \sum_i w(I_u, I_{\ell_i}) \mathbb{I}(I_{\ell_i} \in e), \quad (7)$$

where II is the indicator function, so that $\text{II}(I_{l_i} \in e)=1$ if the labeled image $I_{l_i}$ has been assigned expert rating e in this defect class, and is zero otherwise. The probability of membership $p_e(I_u)$ is computed for each possible expert rating e, and the one with the highest probability is chosen as the Expert Rating for the unlabeled image $I_u$. Rating tool 37 repeats this process is repeated for every unlabeled image, in each defect class. Further exemplary information related to label propagation can be found in X. Zhu and Z. Ghahramani, "Learning from Labeled and Unlabeled Data with Label Propagation." CMU CALD Technical Report CMU-CALD-02-107, 2002, the entire contents of which is incorporated herein by reference.

Returning to FIG. 3, in some exemplary embodiments, after expert 38 has assigned expert ratings to each cluster of images and the labels have been automatically propagated to the remaining images, rating tool 37 allows the expert to explore training data 35 and adjust the label assignments if necessary (68) to ultimately produce expert ratings for the entire set of training data 35. In this way, rating tool 37 provides functionality for automatic subset selection and the subsequent propagation of expert ratings to the larger set of images within training data 35. As a result, rating tool 37 may allow experts 38 to easily manipulate and assign ratings to large datasets (e.g., on the order of tens of thousands of images) even though the images may contain significant redundancy.

Figure 4:
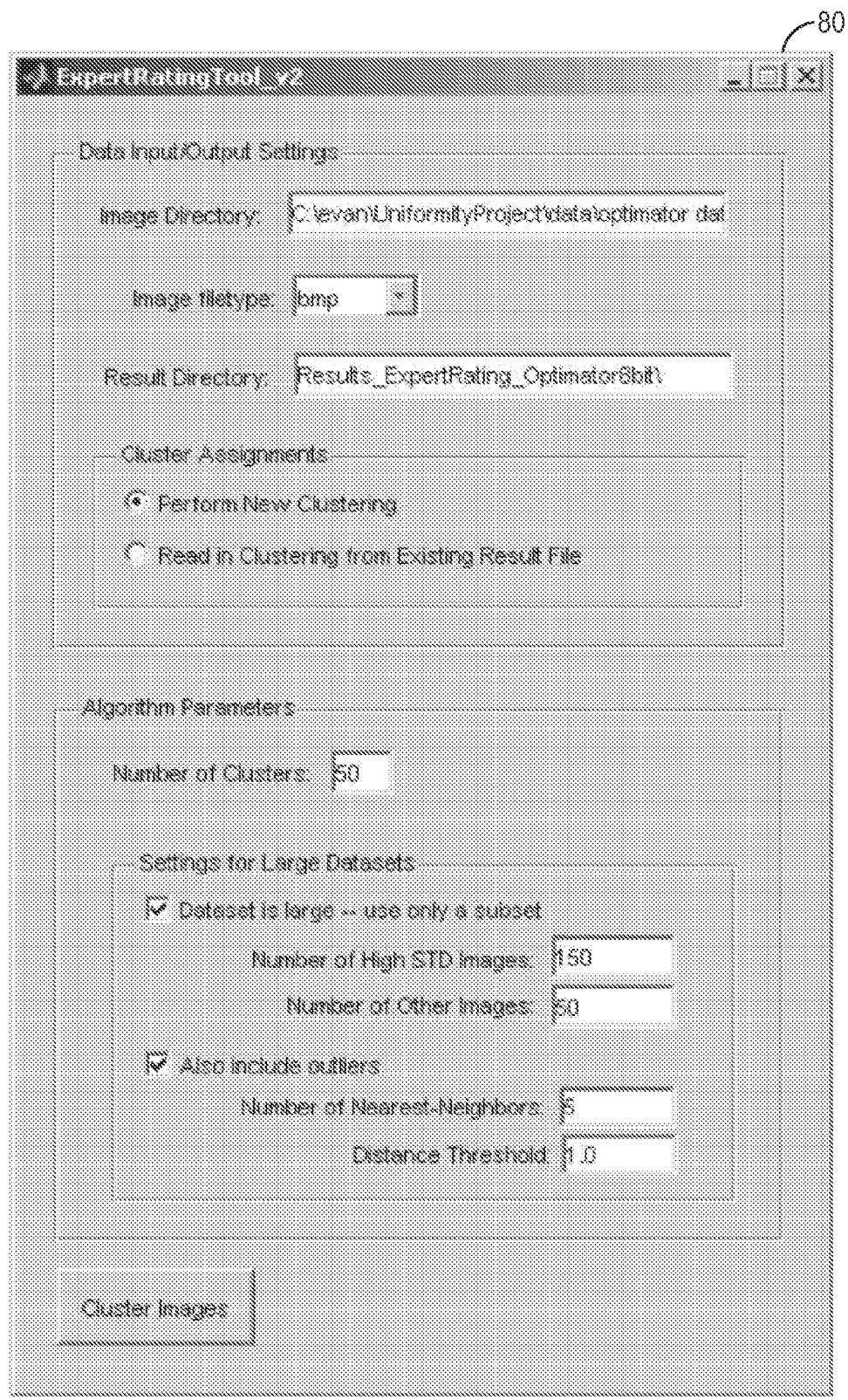

FIG. 4 is an illustration of an exemplary window 80 presented by the user interface of rating tool 37 by which expert 38 configures parameters to control the clustering process. In this example, window 80 includes input mechanisms by which expert 38 specifies a directory of the training images, the format of the training images, a directory for outputting results and a selection indicating whether the rating tool should perform a new clustering of the images or read is input the results from a previous clustering process.

In addition, expert 38 may specify certain parameters for controlling the clustering process. In particular, window 80 includes input fields for specifying the number of clusters into which rating tool 37 is to organize the training images. As described above, rating tool 37 utilizes the desired number of clusters specified by the user to truncate the clustering process upon generating the first linkage tree to have a number of leaf nodes that meet or exceed the specified number of clusters. In addition, expert 38 can specify whether training data 35 is a large dataset and that rating tool 37 should automatically identify a representative subset of images for clustering as described herein. In this case, expert 38 can also specify the parameters for controlling the size of the representative subset $S_0$, i.e., the number $N_1$ of images having the highest variance to include (150 in FIG. 4) and the number $N_2$ of images to randomly select from the remaining images (50 in FIG. 4). This set of $N_1+N_2$ images comprises the initial subset $S_0$. In addition, expert 38 can specify whether rating tool 37 is to include outliers in the representative set $S_1$ and, if so, the number k of nearest-neighbors (kNNs) to examine in feature space for each image (5 in FIG. 4) and the threshold $T_d$ for characterizing the image as an outlier (1.0 in FIG. 4).

Figure 5:
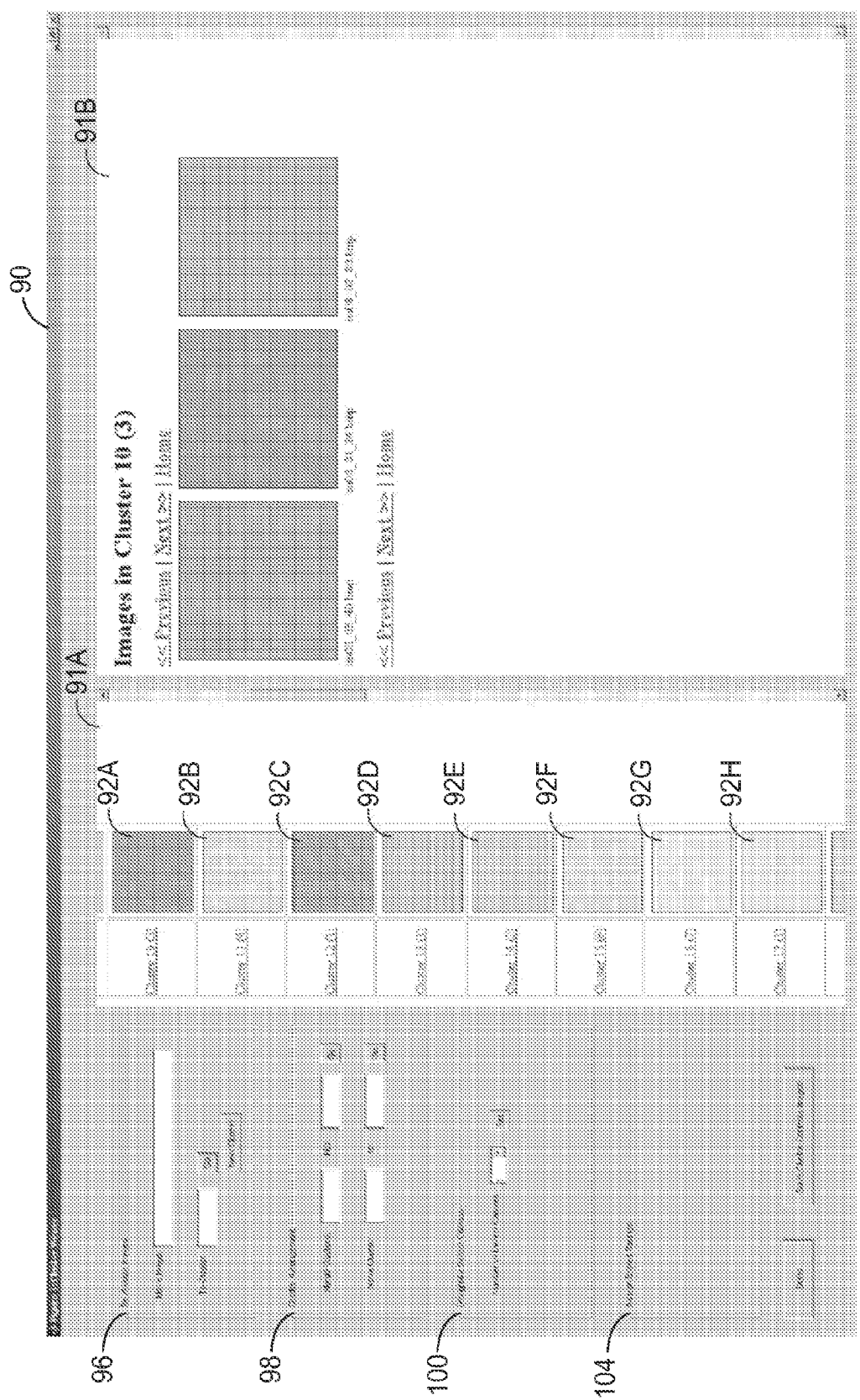

FIG. 5 is an illustration of an example cluster view window 90 presented by rating tool 37 to display the results of the clustering operation. As can be seen, the image clusters are displayed visually in two separate panels 91A, 91B, through which the user can navigate and explore the clusters using the embedded hyperlinks. Left-hand panel 91A provides a high-level overview of the clustering results by displaying a single representative (centroid) image from each clusters 92A-92N. For each cluster, panel 91A displays the representative image, an identifier associated with the cluster and, in parentheses, the number of images assigned to that cluster. For example, cluster 92A has an identifier of "10" and three images have been assigned to the cluster. Rating tool 37 arranges clusters 94A-94N within scrollable panel 91A in accordance with the second agglomerative hierarchical linkage tree described above so that clusters containing similar images are placed in close proximity to one another within the panel. In other words, rating tool 37 may arrange clusters within the scrollable panel 91A in accordance with the leaf nodes of the second agglomerative hierarchical linkage tree.

To explore in more detail, expert 38 can then select (e.g., click on) the representative image or identifier for any of clusters 92 in order to view the images contained therein within right-hand panel 91B. In the example of FIG. 5, expert 38 has selected cluster 92A (i.e., cluster having identifier "10") for review. In this example, panel 91B shows the three images that have been assigned to the cluster and all bear a strong resemblance to one another, indicating that the clustering algorithm appropriately grouped them. Due to the grouping and ordering of the images in subset S1 as presented by panel 91A, expert 28 can explore clustered training data 35 in a very intuitive manner. This may be advantageous over other techniques in which a user may simply be presented with a large unorganized collection of images for manual review and label assignment. The clustering and visualization capabilities described herein may simplify the data exploration task for expert 38, and enable the expert to quickly identify the types of defects present in the representative training data.

As shown in FIG. 5, cluster view window 90 includes input region 96 with which expert 38 interacts to modifying the cluster assignments of individual images, including the ability to move an image to either a different cluster or to a new one. In addition, input region 98 allows the user to interact with the clusters themselves, including the ability to merge two clusters, and the ability to physically move a cluster to a different position in the display order. Rating tool 37 automatically updates display panels 91A, 91B in cluster viewing window 90 in real-time to reflect the changes made in the cluster assignments. In this way, rating tool 37 may be used in a manner that allows expert 38 to have the final say regarding any type of grouping or assignment of the representative images within training data 35. This also provides an extra measure of flexibility in terms of visualization, since ultimately the purpose of the clustering and ordering operations are to provide an enhanced ability to visualize and rate the training data.

In addition, cluster view window 90 includes input region 100 for defining the number of defect classes present within training data 35. Cluster view window 90 also includes input region 104 for assigning expert ratings to the images. Each of input regions 100, 102 are discussed in further detail below.

In certain exemplary embodiments, it may be desirable to provide a user interface with the rating software to receive input from a user specifying one or more classes of defects present within the representative training images. One exemplary user interface is shown in FIG. 6. FIG. 6 shows input region 100 of viewing window 90 in further detail. In this example, expert 38 has indicated that three defect classes exist in the training data based on the review and exploration of clustered training data 35 via cluster viewing window 90. As shown in FIG. 7, once expert 38 sets the number of defect classes, cluster viewing window 90 presents another menu 102 in the same location to allow the user to enter the names of the defect classes which provide a meaningful way to identify them. In the example of FIG. 7, expert 38 has entered names of "chatter," "mottle" and "streaks" for the three types of defect classes identified within training data 35. Display panels 91A, 91B in the cluster viewing window 90 remain open while expert 38 interacts with input region 100 and menu 102, so that the expert still has the option to navigate and visualize the clustered training data while assigning the number of defect classes for the representative training data and names for each of the defect classes.

Figure 8:
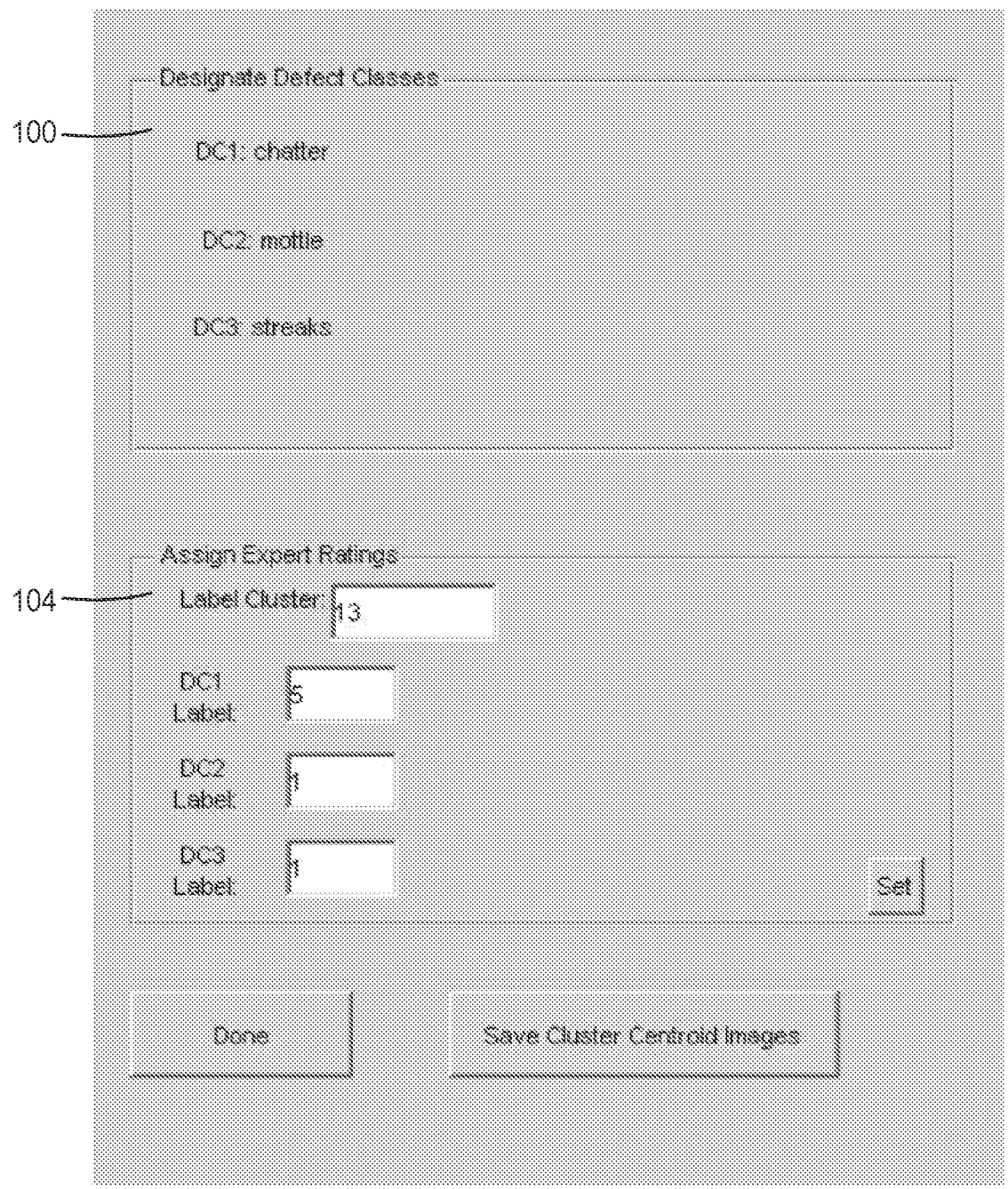

FIG. 8 shows input region 104 of cluster viewing window 90 for assigning expert rating labels to image clusters within the representative subset $S_1$ of training data 35. Once expert 38 has interacted with input region 100 and menu 102 to assign the number and names of the defect classes present in the data, rating tool 37 allows the expert to interact with input region 104 to assign expert ratings to the images of training data 35. In order to greatly simplify this task, rating tool 37 allows expert 38 to assign rating labels to entire clusters, instead of having to label individual images, which could be quite tedious and error-prone. In addition, expert 38 has the option to not label any cluster. In subsequent processing, when the labels are propagated the remaining images not in subset $S_1$, the labels are also propagated to the images in any clusters which are not labeled. As can be seen in FIG. 6, cluster viewing window 90 allows expert 38 to label all defect classes in a cluster simultaneously. For example, in FIG. 6, expert 38 has specified labels of "5," "1" and "1" for the defects "chatter," "mottle" and "streaks" within cluster "13" of the training data. Furthermore, in one example, rating tool 37 puts no restriction on the types of expert ratings that can be assigned. Labels can be numerical, such as the "1" and "5" labels shown here, or they could be textual "acceptable" and rejected" labels. Once expert ratings have been assigned to a cluster, panel displays 91 are updated in real-time to reflect these changes.

Figure 9:
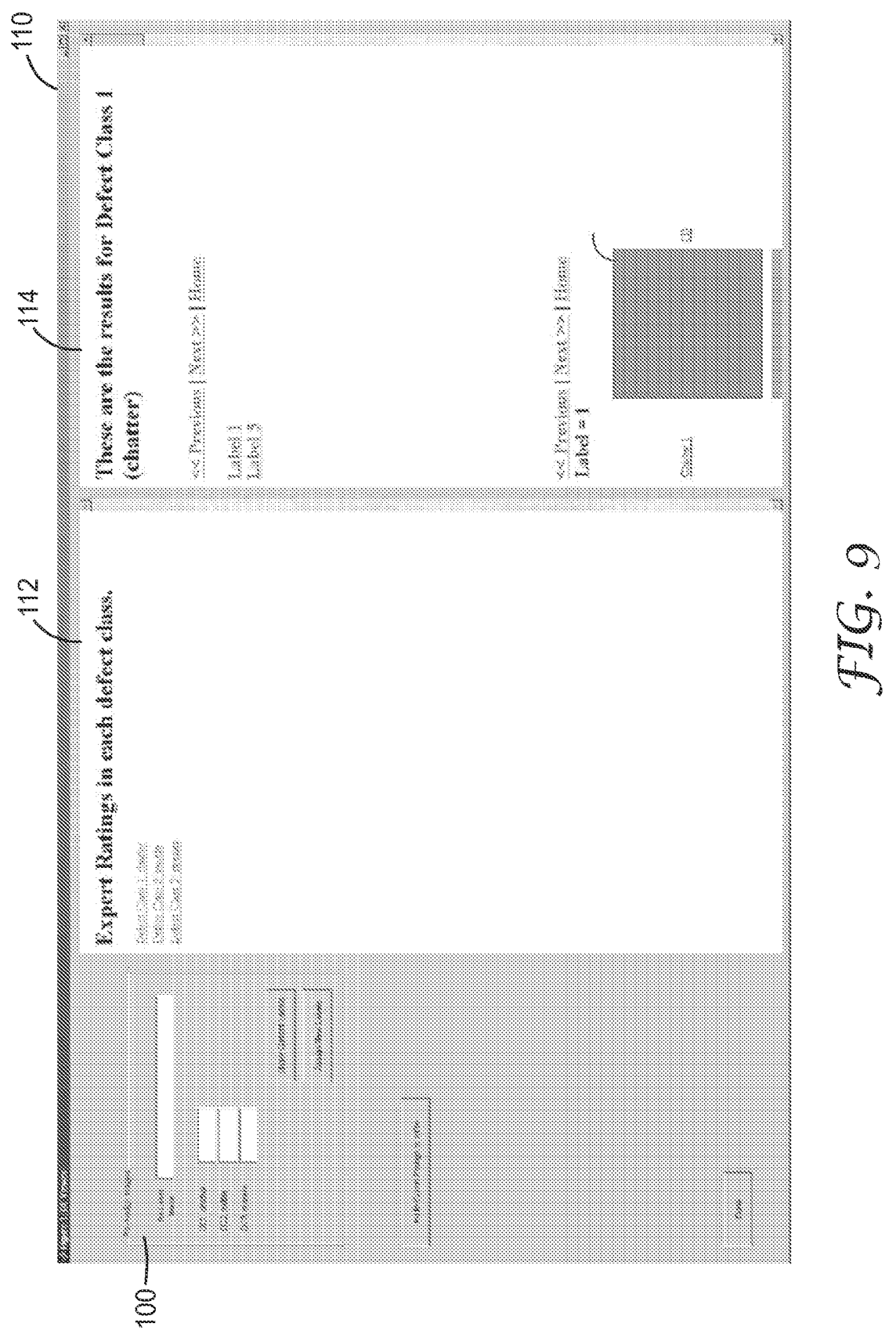

FIG. 9 is an illustration of a final expert rating viewing window 110 presented by rating tool 37 with which expert 38 can visualize and modify the expert ratings in each defect class. Expert rating viewing window 110 displays the final expert rating labels for all images. As shown in FIG. 9, expert rating viewing window 110 contains two side-by-side HTML display panels 112, 114 through which the user can visualize the results by navigating through the pages using the embedded hyperlinks. Expert rating viewing window 110 also contains menu options 120 on the left-hand side for modifying expert ratings.

In terms of visualization, expert rating viewing window 110 displays the results of the labeling process in a way that is intuitive and easy for expert 38 or other users to understand. As one example, expert rating viewing window 110 displays the results for each defect class in a separate HTML page. In each defect class, the images with each possible expert rating are shown within panel 114 as a separate part of the HTML page for that defect class. For example, as shown in FIG. 9, HTML panel 112 lists the defect classes. Upon selection of one of the defect classes, HTML panel 114 shows the images for each possible expert rating. This allows expert 38 to view defects in a cluster independent manner based on the different labels of that defect as assigned to the images. In the example of FIG. 9, the software tool presents the results in "Defect Class 1 (chatter)" starting with the images that have received a label of "1" on the top of the page. HTML panel 114 is vertically scrollable so that expert 38 may review each label utilized for the defect class and, for that label, each image assigned with that label.

To further enhance the user's ability to comprehend the data, rating tool 37 performs another clustering operation to cluster the images within each possible expert rating in a given defect class into relatively small groups of similar images. Rating tool 37 generates HTML panel 114 for the currently selected defect class (e.g., "Defect Class 1 (chatter)") to shows only the centroid image of each cluster, which helps keep only a small, manageable number of images on the display. For example, for label "1" within the "chatter" defect class, rating tool 37 has generated HTML panel 114 to display centroid image 116. Expert 38 can click on the centroid image for each cluster in order to navigate to another HTML page on which all images contained in that cluster are displayed.

With respect to the clustering operation for generating HMTL panel 114, rating tool 37 performs a separate clustering computation within each possible expert rating for every defect class. That is, as described, each image receives an expert rating in every defect class. In other words, each defect class contains all the images, but the images are in general distributed differently among the possible expert ratings in each defect class. For example, a certain image might have an expert rating of "1" in the defect class "chatter", but an expert rating of "5" in the defect class "mottle." Rating tool 37 performs separate clusterings so as to compute independent linkage trees for each label of each defect class. As one example, rating tool 37 may compute clusterings in defect class "chatter" for the images with expert Rating "1" and those with the expert rating "5," and likewise in the other defect classes.

In one exemplary embodiment, the clusters are computed as follows. The set of images with expert rating e in defect class c is referred to as $S_e^c$. The set $S_e^c$ is made up of both images from the initial subset $S_1$, as well as other images from $\overline{S_1}$ to which the expert ratings were propagated. Images $S_e^c \cap S_1$ represent the images with expert rating e in defect class c that were in the initial subset $S_1$ that we labeled previously. Since the images in $S_1$ were clustered previously, each image in $S_e^c \cap S_1$ has already been assigned to a cluster. Rating tool 37 uses these cluster assignments to initialize the clustering of $S_e^c \cap S_1$. That is, this is used as an initial clustering to start the process, then these clusters are modified as new images are added to them sequentially. For each image in $S_e^c \cap \overline{S_1}$ (i.e., the images in $S_e^c$ that do not already have cluster assignments), we assign it to the cluster in $S_e^c \cap S_1$ to which it is closest. This procedure is more efficient than computing an entirely new clustering for each set $S_e^c$, since it exploits our previous clustering of $S_1$, and clusters the remaining images $S_e^c \cap \overline{S_1}$ incrementally.

Expert rating viewing window 110 also includes menu options 120 on the left-hand side for modifying expert ratings for any image by entering the image name. Using menu options 120, the user can both view the current expert ratings of an image in all defect classes, as well as change them if necessary.

Various embodiments of the invention have been described. These and other embodiments are within the scope of the following claims.

The invention claimed is:

1. A method comprising:
   executing rating software on a computer to extract features from each of a plurality of training images by computing a numerical descriptor for each of the training images from pixel values of the respective training image;
   processing the numerical descriptors of the training images with the rating software to automatically select a representative subset of the training images;
   performing a first clustering process with the rating software to process the numerical descriptors of the representative subset of the training images and compute a plurality of image clusters for the representative subset of training images;
   receiving input from at least one of a user or the computer assigning an individual rating label to each of the plurality of image clusters for each of a specified classes of defects,
      wherein receiving input from the user further comprises presenting a user interface with the rating software to receive input from the user specifying one or more classes of defects present within the plurality of training images, and optionally
      wherein receiving input from the computer further comprises using the computer to determine a number of defect classes present within the representative training images and assign a severity label to each of the plurality of image clusters for each of the specified classes of defects; and
   for each of the image clusters, automatically propagating, with the rating software, each of the individual rating labels assigned to the classes of defects for the image cluster to all of the training images within that image cluster.

2. The method of claim 1, further comprising automatically assigning, with the rating software, rating labels to all remaining ones of the training images not included within the representative subset of the training images for each of the classes of defects, optionally wherein automatically assigning rating labels with the rating software comprises, for each of the unlabeled training images not included within the representative subset of the training images:
   computing a pair-wise distance for the numerical descriptor of the unlabeled training image to the numerical descriptor of each of the labeled images within the representative subset of the training images;
   computing a set of probabilities for each specified classes of defects, wherein the set of probabilities for each class of defects includes a probability for each of the rating labels specified for the class of defect and indicates the probability that the unlabeled training image is a member of the training images that have been assigned that particular rating label for that particular class of defect; and
   assigning to the unlabeled training image the rating labels having the highest probability within each of the classes of defects.

3. The method of claim 1, wherein computing a numerical descriptor for each of the training images comprises one of (a), (b) or (c):
   (a) for each of the training images, computing a feature vector at each of the pixels of the training image based on one or more derivatives of intensity values of the pixel relative to a plurality of neighboring pixels, and computing a covariance matrix for the training image based on the feature vectors for each of the pixels of the training image;
   (b) for each of the training images, convolving the pixel values of the training image with one or more filters to compute the numerical descriptor for the training image; or (c) for each of the training images, computing a histogram of intensity values of the pixels of the training image and computing the numerical descriptor for the training image from the histogram of intensity values.

4. The method of claim 1, wherein automatically selecting a representative subset of the training images comprises one of (a) or (b):
  (a) processing the numerical descriptors of the training images with the rating software to compute a pixel intensity variance for each of the training samples, and identifying with the rating software a first subset of the training images having the highest pixel intensity variances to include in the representative subset of training images; or
  (b) executing the rating software to randomly select a second subset from the training images remaining after selecting the first subset and computing the representative subset to include the second subset of the training images.

5. The method of claim 4, wherein automatically selecting a representative subset of the training images comprises (b), and further comprises presenting a user interface of the rating software to receive a first configurable parameter specifying a target size of training images for the first subset of training images and a second configurable parameter specifying a target size for the second subset of training images.

6. The method of claim 5, wherein automatically selecting a representative subset of the training images further comprises, for each of the training images not included in the first subset or the second subset:
  identifying, with the rating software, a plurality of nearest neighbor numerical descriptors for the training image in a feature space associated with the numerical descriptors;
  computing a distance to each of the nearest neighbors for the numerical descriptor of the training image; and
  including the training image within the representative subset when all of the distances to the nearest neighbors of the training image exceed an outlier threshold that indicates the training image is an outlier training image.

7. The method of claim 6, further comprising presenting a user interface of the rating software to receive a first configurable parameter specifying the number of nearest neighbors to identify when determining whether a training image is an outlier training image and a second configurable parameter specifying the outlier threshold.

8. The method of claim 1, further comprising presenting a user interface of the rating software to receive input from the user specifying whether the training images constitute a large dataset and directing the rating software to automatically identify the representative subset of the training images for clustering.

9. The method of claim 1, wherein performing a first clustering process with the rating software comprises processing the numerical descriptors of the representative subset of the training images to compute the plurality of the image clusters.

10. The method of claim 9, wherein computing a hierarchy comprises:
  presenting a user interface to receive input from the user specifying a desired number of the image clusters;
  applying a bottom-up agglomerative clustering algorithm to the representative subset of training images to form a tree in accordance with the numerical descriptors for each of the training images within the representative subset; and
  truncating the clustering process upon generating the tree to have a number of leaf nodes that at least meets the desired number of the image clusters specified by the user.

11. The method of claim 9, further comprising:
  computing an order for the image clusters based on similarity between images of the image clusters;
  presenting a user interface with the rating software that displays the plurality of image clusters and includes input mechanisms that allows the user to navigate the plurality of image clusters based on the ordering; and
  controlling display of the image clusters within the user interface in accordance with the computed order so that more similar image clusters are displayed more closely to one another on the user interface than dissimilar image clusters.

12. The method of claim 11, wherein computing an order for the image clusters comprises:
  for each pair of the image clusters, processing the numerical descriptors to compute individual distances between each image within a first image cluster of the pair and each image within a second image cluster of the pair;
  computing a median of the individual distances to determine an inter-cluster distance for each of the pair of image clusters; and
  computing the order as a second tree to order the image clusters based on the pair-wise inter-cluster distances.

13. The method of claim 12, wherein presenting a user interface with the rating software that allows the user to view and navigate the plurality of image clusters comprises using an arrangement of leaf nodes of the second tree to control the display of the plurality of image clusters within the user interface.

14. The method of claim 12, wherein presenting a cluster view window within the user interface of the rating software comprises:
  displaying a single representative image from each cluster;
  receiving input from the user selecting the representative image for one of the image clusters; and
  in response to the selection, updating the user interface to display the training images assigned to the corresponding image cluster.

15. The method of claim 14, further comprising arranging the clusters within a scrollable panel in accordance with the second hierarchy.

16. The method of claim 11, further comprising:
  presenting the user interface to include an input mechanism to receive input from the user identifying two of the image clusters to be merged;
  in response to receiving input, modifying the plurality of image clusters by merging the training images of the two image clusters identified by the user into a single cluster; and
  updating the user interface to display the modified plurality of image clusters.

17. The method of claim 11, further comprising:
  presenting the user interface to include an input mechanism to receive input from the user identifying one or more of the training images to be reassigned from a first one of the image clusters to a second one of the image clusters;
  in response to receiving input, modifying the plurality of image clusters by reassigning the one or more training images to the second cluster; and
  updating the user interface to display the modified plurality of image clusters.

18. The method of claim 11, further comprising:
performing a second clustering process to compute a plurality of hierarchies of image clusters, each of the hierarchies clustering the training images assigned with a respective one of the rating labels for a respective one of the classes of defect; and
presenting the user interface to include an input mechanism to receive input selecting one of the classes of defects;
upon receiving the input, presenting the user interface to display the hierarchies of image clusters for the rating labels of the selected class of defect, wherein the user interface includes input mechanisms that allows the user to navigate the hierarchies of image clusters associated with each of the rating labels for the selected class of defect, optionally wherein performing a second clustering process comprises utilizing the cluster assignments determined during the first clustering process to initialize the image clusters of the second clustering process.

19. An apparatus comprising:
a processor;
a memory storing a plurality of training samples;
rating software executing on the processor, wherein the rating software includes a feature extraction module to extract features from each of a plurality of training images by computing a numerical descriptor for each of the training images from pixel values of the respective training image, and wherein the rating software performs a first clustering process to process the numerical descriptors of the training images to automatically select a representative subset of the training images and compute a plurality of image clusters for the representative subset of training images; and
at least one of the rating software executing on the processor or a user interface presented by the rating software and having input mechanisms to receive input from a user, specifying one or more classes of defects present within the representative training images and a set of individual rating labels for each of the classes of defects,
wherein the user interface further includes input mechanisms to receive input assigning an individual rating label to each of the image clusters for each of the specified classes of defects,
and optionally wherein the rating software executing on the processor specifies a number of defect classes present within the representative training images, and assigns a severity label to each of the plurality of image clusters for each of the specified classes of defects; and
wherein, for each of the image clusters, the rating software automatically propagates each of the individual rating labels assigned to the classes of defects for the image cluster to all of the training images within that image cluster, optionally wherein the rating software automatically assigns rating labels to all remaining ones of the training images not included within the representative subset of the training images for each of the classes of defects.

20. A system comprising:
a server executing a rating software, wherein the server comprises:
a processor;
a memory storing a plurality of training samples;
rating software executing on the processor, wherein the rating software includes a feature extraction module to extract features from each of a plurality of training images by computing a numerical descriptor for each of the training images from pixel values of the respective training image, and wherein the rating software performs a first clustering process to process the numerical descriptors of the training images to automatically select a representative subset of the training images and compute a plurality of image clusters for the representative subset of training images;
wherein at least one of the rating software executing on the processor or a user interface presented by the rating software specifies one or more classes of defects present within the representative training images and a set of individual rating labels for each of the classes of defects,
further wherein the user interface comprises an input mechanism to receive input from a user assigning an individual rating label to each of the image clusters for each of the specified classes of defects, and
optionally wherein the rating software executing on the processor specifies a number of defect classes present within the representative training images, and assigns a severity label to each of the plurality of image clusters for each of the specified classes of defects,
wherein, for each of the image clusters, the rating software automatically propagates each of the individual rating labels assigned to the classes of defects for the image cluster to all of the training images within that image cluster, and
further wherein the rating software executes a training phase to compute a classification model based on the rating labels assigned to the training images; and
a computerized inspection system to scan sequential portions of a web material to acquire samples, wherein the computerized inspection system applies classifiers to assign a rating to each of the samples in accordance with the classification model.

* * * * *

UNITED STATES PATENT AND TRADEMARK OFFICE
CERTIFICATE OF CORRECTION

PATENT NO.       : 8,965,116 B2                                  Page 1 of 1
APPLICATION NO.  : 13/877545
DATED            : February 24, 2015
INVENTOR(S)      : Evan Ribnick et al.

It is certified that error appears in the above-identified patent and that said Letters Patent is hereby corrected as shown below:

IN THE SPECIFICATION

Column 8
Line 62, delete "an" and insert -- and --, therefor.

Column 14
Line 6 (approx.), delete " )❙( " and insert -- )❙( --, therefor.

Signed and Sealed this
Thirteenth Day of October, 2015

Michelle K. Lee
*Director of the United States Patent and Trademark Office*